US00PP09859P

United States Patent [19]

Zaiger et al.

[11] Patent Number: Plant 9,859

[45] Date of Patent: Apr. 15, 1997

[54] APRICOT TREE "EARLISUNRISE"

[76] Inventors: Chris F. Zaiger, 929 Grimes Ave.; Gary N. Zaiger, 1907 Elm Ave.; Leith M. Gardner, 1207 Grimes Ave.; Grant G. Zaiger, 4005 California Ave., all of Modesto, Calif. 95358

[21] Appl. No.: 593,456

[22] Filed: Jan. 29, 1996

[51] Int. Cl.[6] ..... A01H 5/00

[52] U.S. Cl. ..... Plt./39

[58] Field of Search ..... Plt./39

*Primary Examiner*—James R. Feyrer

[57] ABSTRACT

A new and distinct variety of apricot *Prunus armeniaca*, tree, which has the following unique combination of the features that are desirable in a new variety:

1. Early maturity of fruit.
2. Fruit with good flavor and eating quality.
3. Heavy and regular production.
4. Vigorous, semi-spreading growth.
5. Fruit with firm flesh, good handling and shipping quality.

1 Drawing Sheet

ORIGIN OF THE VARIETY

The present new and distinct variety of apricot tree was developed by us in our experimental orchard located near Modesto, Calif., as a second generation seedling from a cross between two selected seedlings, field identification numbers 78EB575 and 123GD161. The maternal parent (78EB575), originated as a seedling selection from seedlings grown from an open pollinated Spring Giant Apricot (U.S. Plant Pat. No. 5,138) seeds. The paternal parent (123GD161), originated as a seedling selection from seedlings grown from open pollinated Earlicot Apricot (U.S. Plant Pat. No. 7,198) seeds. A large number of these second generation seedlings were planted and grown under careful observation by us. One such seedling, which is the present variety, having especially desirable fruit characteristics, was selected for asexual reproduction and commercialization.

ASEXUAL REPRODUCTION OF THE VARIETY

The present new variety of apricot tree was asexually propagated by budding, as performed by us in our experimental orchard located near Modesto, Calif., shows that all said characteristics run true to form and are established and transmitted through succeeding asexual propagations and come true to the original tree in all respects.

SUMMARY OF THE VARIETY

The herein described new variety of apricot tree is of large size; vigorous, semi-spreading growth; and is a productive and regular bearer of early maturing, medium size, firm, yellow flesh, freestone fruit with good handling and shipping quality. The fruit is further characterized as having good flavor and eating quality, and being relatively uniform in ripening throughout the tree. In comparison to Earlicot Apricot to U.S. Plant Pat. No. 7,198), the new variety is approximately 10 to 11 days earlier in maturity.

DESCRIPTION OF THE PHOTOGRAPH

The accompanying photographic illustration shows typical specimens of the foliage and fruit of the new variety of apricot tree. The illustration depicts the upper and lower surface of the leaves, an exterior and sectional view of the fruit divided in the suture plane to show flesh coloration, pit cavity and a stone remaining in place. The photographic illustration was taken shortly after the fruit was picked at maturity (shipping ripe), and the colors are as nearly true as reasonably possible in a color representation of this type.

DESCRIPTION OF THE VARIETY

The following is a botanical detailed description of the new variety of apricot tree, its flowers, foliage and fruit, based on observations of specimens grown in our experimental orchard located near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Density.*—Medium dense.
- *Growth.*—Semi-spreading.
- *Productivity.*—Productive.
- *Bearing.*—Regular.

Trunk:
- *Size.*—Large.
- *Texture.*—Medium shaggy.
- *Color.*—Brown to dark brown (6-E-8) to (6-F-8).

Branches:
- *Size.*—Medium.
- *Texture.*—Smooth to medium rough. Varies with age of growth.
- *Lenticels.*—Numerous. Medium size.
- *Color.*—Light brown to brown (6-D-7) to (6-E-7).

Leaves:
- *Size.*—Large. Average length 4⅞". Average width 3¼".
- *Form.*—Ovate, pointed.
- *Texture.*—Smooth.
- *Margin.*—Serrate.
- *Petiole.*—Medium length. Medium thickness.
- *Glands.*—Number varies from 1 to 3. Average number 2. Small size. Globose. Located on base of leaf blade and upper portion of petiole.

Flower buds:
- *Size.*—Medium.
- *Form.*—Plump.
- *Length.*—Medium.

Flowers:
- *Size.*—Large.
- *Blooming period.*—Feb. 20, 1994 to Feb. 26, 1994. Varies slightly with climatic conditions.
- *Pollen.*—Present.
- *Color.*—Pink.
- *Pubesence.*—Pubescent.

Fruit:
- *Maturity when described.*—Firm ripe.

*Date of first picking.*—May 7, 1994.
*Date of last picking.*—May 12, 1994.
*Size.*—Medium, comparatively uniform. Average diameter axially 1¾" to 2". Average diameter transversely in suture plane 1⅝" to 1⅞". Average diameter measured at right angles to suture plane 1⅝" to 1⅞".
*Form.*—Nearly globose, slightly flattened in suture plane.
*Suture.*—Shallow, extends from base to apex.
*Ventral surface.*—Slightly lipped, varies from rounded to slightly lipped.
*Cavity.*—Rounded to slightly elongated in suture plane. Average depth ⅜". Average breadth ½".
*Base.*—Retuse.
*Apex.*—Slightly retuse, varies from slightly retuse to rounded.

Flesh:
*Color.*—Yellow to sunflower yellow (4-A-5) to (4-A-7).
*Ripens.*—Evenly.
*Texture.*—Firm.
*Juice.*—Moderate.
*Fibers.*—Few, small, tender.
*Flavor.*—Good.
*Eating quality.*—Good.
*Amygdalin.*—Undetected.
*Aroma.*—Slight.

Skin:
*Color.*—Yellow to golden yellow ground color (5-A-7) to (5-A-8). Reddish orange blush (7-B-8) to (7-C-8) on fruit exposed to sun.
*Thickness.*—Medium.
*Texture.*—Medium, tenacious to flesh.
*Tendency to crack.*—None.
*Down.*—Scant, very short.

Stone:
*Type.*—Freestone.
*Size.*—Medium to large. Average length — 1" to 1⅛". Average breadth — ⅞" to 1". Average thickness — ½" to ⅝.
*Form.*—Ovoid.
*Base.*—Usually rounded, varies from rounded to straight.
*Apex.* —Nearly rounded, varies form rounded to slight pistil point.
*Sides.*—Usually equal, varies from equal to unequal.
*Surface.*—Slightly pitted throughout.
*Ridges.*—Two small ridges, extending on each side of suture.
*Tendency to split.*—Very slight.
*Color.*—Varies from yellowish brown to brown (5-E-4) to (5-F-4).

Use: Dessert.
*Market.*—Local and long distance.
Keeping quality: Good.
Shipping Quality: Good.

The new variety of apricot tree, its flowers, foliage and fruit, may vary in slight detail due to climate, soil conditions, and cultural practices under which the variety may be grown; the present description is that of the variety grown under the ecological conditions prevailing near Modesto, Calif.

We claim:

1. A new and distinct variety of apricot tree, substantially as illustrated and described, characterized by its large size, vigorous and semi-spreading growth, and is a productive and regular bearer of medium size, yellow flesh, freestone fruit with good flavor and eating quality; the fruit is further characterized by having firm flesh with good handling and shipping quality and, in comparison to Earlicot Apricot (U.S. Plant Pat. No. 7,198), is approximately 10 to 11 days earlier in maturity.

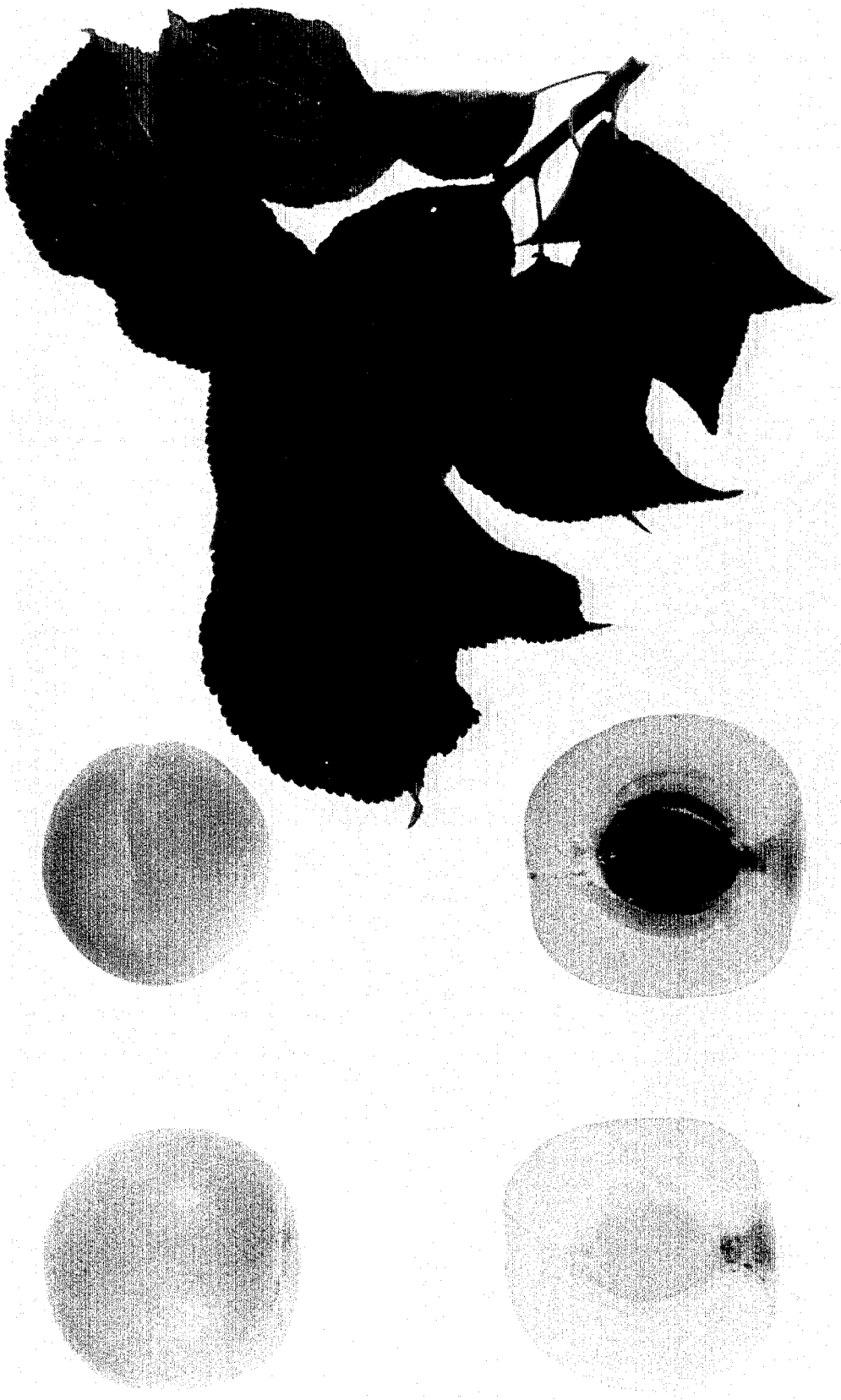

* * * * *